United States Patent [19]  [11] 4,366,168
Clinton, deceased et al.  [45] Dec. 28, 1982

[54] ANTICOCCIDIAL COMBINATIONS

[75] Inventors: Albert J. Clinton, deceased, late of Indianapolis, Ind., by American Fletcher National Bank and Trust Company, Administrator; George O. P. O'Doherty, Greenfield, Ind.

[73] Assignee: Eli Lilly and Company, Indianapolis, Ind.

[21] Appl. No.: 304,403

[22] Filed: Sep. 21, 1981

[51] Int. Cl.³ .................. A61K 31/35; A61K 31/135
[52] U.S. Cl. .................................... 424/283; 424/115; 424/181; 424/330
[58] Field of Search ............... 424/330, 115, 181, 283

[56] References Cited

U.S. PATENT DOCUMENTS 3,627,883 12/1971 Gorman et al. ............... 424/122
4,218,438 8/1980 Callender et al. ............. 424/115
4,304,791 12/1981 Clinton .......................... 424/330
4,311,710 1/1982 Clinton .......................... 424/330

FOREIGN PATENT DOCUMENTS 156 1/1979 European Pat. Off.
4642 10/1979 European Pat. Off.

*Primary Examiner*—Sam Rosen
*Attorney, Agent, or Firm*—Charles W. Ashbrook; Arthur R. Whale

[57] ABSTRACT

Combinations of a polyether antibiotic and a 2,4-dinitro-N-[4-(fluoroalkoxy)phenyl]-6-(trifluoromethyl)benzenamine are synergistic in controlling coccidiosis in animals.

17 Claims, No Drawings

ANTICOCCIDIAL COMBINATIONS

BACKGROUND OF THE INVENTION

This invention concerns combinations of a polyether antibiotic and a benzenamine. The combinations are synergistic in the treatment of coccidial infections.

All of the compounds employed in the combinations of this invention are known in the art. The polyether antibiotics are a class of compounds that have been widely used in the control of coccidiosis in poultry. The most widely used polyether antibiotic anticoccidial agent is monensin sodium, U.S. Pat. No. 3,501,568. The polyether antibiotics recently have been reported to be synergistic with nicarbazin and 4,4'-dinitrocarbanilide in the treatment of coccidiosis in poultry, U.S. Pat. No. 4,218,438.

The second component of the combinations provided by this invention is a 2,4-dinitro-N-[4-(fluoroalkoxy)-phenyl]-6-(trifluoromethyl)benzenamine. These compounds are disclosed as antifungal agents in U.S. application Ser. No. 110,308, now U.S. Pat. No. 4,304,791 and European Application No. 156. U.S. application Ser. No. 110,307, now U.S. Pat. No. 4,311,710 describes the use of these compounds in the treatment of coccidial infections.

While the components employed in the combinations of this invention are known to have anticoccidial activity, there is nothing in the art to suggest that together the components would be synergistic. It is therefore an object of this invention to provide a synergistic anticoccidial combination, and a method for controlling coccidiosis in poultry employing such combination.

SUMMARY OF THE INVENTION

This invention provides anticoccidial combinations comprised of
  (a) a polyether antibiotic and
  (b) a benzenamine selected from 2,4-dinitro-N-[4-(trifluoromethoxy)phenyl]-6-(trifluoromethyl)benzenamine, 2,4-dinitro-N-[4-(1,1,2,2-tetrafluoroethoxy)-phenyl]-6-(trifluoromethyl)benzenamine or 2,4-dinitro-N-[4-(pentafluoroethoxy)phenyl]-6-(trifluoromethyl)-benzenamine. The respective components will be present in a synergistic anticoccidial ratio which is from about 1 to about 10 parts by weight of the polyether antibiotic (a) to about 10 to about 1 part by weight of the benzenamine (b).

The present invention also provides a method for controlling coccidosis in poultry comprising the oral administration to the poultry of a feedstuff comprising the combination of the invention. Also provided are compositions to be employed in the foregoing method.

DETAILED DESCRIPTION OF THE INVENTION

The polyether antibiotics are a class of compounds produced by the Streptomyces genus of microorganisms. They are characterized by comprising a multiplicity of cyclic ethers in their structure. The class of compounds is reviewed in Kirk-Othmer: *Encyclopedia of Chemical Technology*, Vol. 3, Third Edition (John Wiley & Sons, Ind. 1978), page 47 et seq.; in *Annual Reports in Medicinal Chemistry*, Vol. 10, (Academic Press, N.Y. 1975), page 246 et seq.; and in *J. Chrom. Lib.*, Vol. 15 (Elsevier Scientific Publishing Co., N.Y., 1978), page 488 et seq.

As with most products of fermentation, the polyether antibiotics generally comprise more than one factor. The combinations of this invention include the various individual factors as well as mixtures thereof. Also, many of the polyether antibiotics form derivatives such as esters, ethers, salts, amides, or the like, and these generally are active themselves or are readily converted in vivo to an active form of the antibiotic. Accordingly, all such derivatives are usable in combinations of this invention. All that is necessary is that an active moiety of a polyether antibiotic be delivered in vivo so as to reach the site of coccidial infection.

Typical of the polyether antibiotics to be employed in the combinations of this invention are the following. Monensin, which includes principal factors A, B and C and salts thereof, as described in U.S. Pat. No. 3,501,568. Several derivatives of monensin have been disclosed, for instance in U.S. Pat. No. 3,832,358 and European Pat. No. 11,859. A particularly preferred combination of this invention is monensin, primarily factors A and B, as the sodium salt, together with a benzenamine, particularly the tetrafluoroethoxy benzenamine. Also preferred is the combination of the 4-bromophenylurethan of monensin described in EP 11,859, together with a benzenamine.

Polyether antibiotics A204, lasalocid (X-537A), dianemycin, nigericin and X-206 are described in U.S. Pat. No. 3,794,732. A number of derivatives of lasalocid are described in U.S. Pat. Nos. 3,944,573 and 4,247,690.

Ionomycin is a polyether antibiotic obtained by cultivating the microorganism *Streptomyces conglobatus* ATCC No. 31005. The production of ionomycin and its properties are described in U.S. Pat. No. 3,873,693.

Laidlomycin is a polyether antibiotic described by Kitame et al. in *J. Antibiot*, 27, 884–888 (1974).

Grisorixin is the name assigned to deoxynigericin, and is described in French Pat. No. 2,097,053. As noted above, nigericin is disclosed in U.S. Pat. No. 3,794,732.

Lenoremycin, also referred to as "antibiotic A-130A" is a polyether antibiotic produced by *Streptomyces hydroscopicus* ATCC No. 21840. The properties of lenoremycin are detailed in U.S. Pat. No. 3,903,264.

U.S. Pat. Nos. 4,038,384 and 4,085,224 describe the preparation and use of narasin and salinomycin. Narasin is referred to therein as "A-28086".

Lonomycin is a polyether also known as "antibiotic TM481", "antibiotic DE 3936" and "emericid". Its preparation and use are described in *J. Antibiotics*, 29, No. 1, 15-20 (1976). Derivatives of lonomycin are disclosed in U.S. Pat. No. 4,199,515.

Alborixin, also known as "S14750/A" is derived from *Streptomyces hygroscopicus* NRRL 5077 and is described in British Pat. No. 1,541,485.

Septamycin is a polyether produced by cultivating *Streptomyces albus* NRRL 3883. This compound was initially referred to as "A28695A" and "A28695B", as well as "BL580". Its properties are described in U.S. Pat. Nos. 3,839,558 and 4,189,537.

Etheromycin is also known as "antibiotic 38295" and "CP38295". It is disclosed in U.S. Pat. No. 4,129,578.

Mutalamycin is a polyether derivative of lonomycin and is described in Belgian Pat. No. 845,708. It is also referred to as "S11743A".

Antibiotic A-23187 is described in U.S. Pat. No. 3,923,823. It is also known as "Ionophore A23187" and "Calcimycin".

Preferred polyether antibiotics to be employed in the combinations of this invention include monensin, monensin phenylurethan derivatives, narasin, lasalocid, salinomycin, A-204, Ionomycin, X-206, nigericin, and dianemycin.

The benzenamine that is component (b) in the present combinations is a compound having the structure

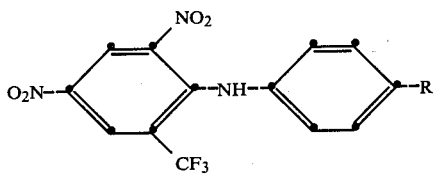

wherein R is OCF$_3$, OCF$_2$CF$_2$H or OCF$_2$CF$_3$. These compounds can be prepared by reacting approximately equimolar quantities of 2,4-dinitro-6-trifluoromethylphenyl chloride and a 4-(fluoroalkoxy)phenylamine in a suitable solvent such as ethanol and in the presence of an acid scavenger such as triethylamine. The compounds are disclosed in U.S. application Ser. No. 110,308.

According to this invention, a polyether antibiotic and a benzenamine are employed in amounts which, in combination, are synergistic in the treatment of at least one coccidiosis-causing organism. The combination is synergistic when employed in amounts of about 1 to about 10 parts by weight of polyether and about 10 to about 1 part by weight of benzenamine. The invention will typically be practiced in treating coccodiosis in poultry, and the treatment is generally accomplished by orally administering to the poultry to be treated a poultry feedstuff comprising from about 5 to about 125 parts per million (ppm) of the benzenamine, and an amount of a polyether antibiotic which, in combination with the benzenamine, is synergistic, for instance to at least one coccidiosis-causing strain of Eimeria. Exemplary amounts of typical polyether antibiotics to be employed are:

from about 20 to about 120 ppm of monensin;
from about 25 to about 100 ppm of narasin;
from about 35 to about 125 ppm of lasalocid;
from about 25 to about 100 ppm of salinomycin
from about 1 to about 500 ppm of A-204;
from about 50 to about 100 ppm of dianemycin;
from about 40 to about 80 ppm of ionomycin;
from about 10 to about 120 ppm of monensin factor A, 4-nitrophenylurethan;
from about 30 to about 200 ppm of laidlomycin;
from about 15 to about 95 ppm of grisorixin;
from about 25 to about 150 ppm of 1-(phenylthiomethyl)-1-descarboxylasolocid;
from about 20 to about 95 ppm of lenoremycin;
from about 15 to about 150 ppm of mutalomycin;
from about 50 to about 200 ppm of nigericin;
from about 10 to about 120 ppm of X-206.

While a preferred embodiment of the invention is a combination wherein a single polyether antibiotic and a benzenamine are the sole anticoccidial agents, a combination can contain more than one polyether antibiotic and more than one benzenamine. For example, a combination of the invention may comprise about 1 part by weight of a benzenamine, about 5 parts by weight of lasalocid, and about 5 parts by weight of salinomycin. The most preferred combination of the invention is, however, about 1 to 2 parts by weight of benzenamine and from about 1 to about 10 parts by weight of monensin, especially monensin factors A and B as the sodium salts. A particularly preferred composition for feeding to poultry according to this invention is one containing from about 5 to about 50 ppm of a benzenamine and from about 30 to about 80 ppm of commercially available monensin. The most preferred benzenamine to be employed in the combinations of this invention is 2,4-dinitro-N-[4(1,1,2,2-tetrafluoroethoxy)phenyl]-6-(trifluoromethyl)benzenamine.

In a further embodiment of this invention there is provided a method for treating and controlling coccidiosis in animals. This method may be practiced for the prophylactic control of coccidiosis, for instance by the routine and continued administration to an animal susceptible to coccidiosis of an effective dose of a combination as provided herein, as well as for the therapeutic treatment of coccidiosis in animals so infected. The components (a) and (b) can be formulated and/or administered individually, but preferably are formulated together for convenient administration to animals by any of a number of routes, including the oral, intramuscular, intravenous, subcutaneous and related routes. The compounds are preferably formulated for systemic administration to animals such as bovine. As already noted, a preferred method according to the invention comprises treating poultry for coccidial infections. The combinations defined above are especially useful in treating and in aiding in the prevention of coccidiosis in poultry caused by Eimeria necatrix, E. tenella, E. acervulina, E. brunetti, E. mivati, and E. maxima. The method of this invention is ideally suited to the prevention of coccidiosis in broiler chickens.

For treatment of poultry according to this invention, the combinations are preferably formulated for oral administration, for instance as a feedstuff, by addition to the normal daily feed ration of the animals. Ideally, the anticoccidial combinations will be uniformly dispersed throughout a finished animal feed mixture. Such medicated feed mixture is then administered ad lib to animals such as chickens and turkeys. The normal concentration of combination to be employed in a feedstuff will be from about 20 grams per ton to about 500 grams per ton (g/T), and more preferably about 100 g/T to about 300 g/T. Poultry will routinely consume about 5 to about 250 grams of such feedstuff per day, depending upon size and age of the bird.

Any of a number of poultry feedstuffs can be utilized as a suitable carrier or diluent for the combinations defined above. Typical feedstuffs include the following

| Ingredients | Percent |
|---|---|
| Broiler Starter | |
| Corn, Yellow, Ground | 50.0 |
| Soybean Oil Meal, Solvent Extracted, Dehulled (50%) | 30.9 |
| Animal Fat | 6.5 |
| Fish Meal with Solubles (60%) | 5.0 |
| Corn Distillers Dried Solubles | 4.0 |
| Dicalcium Phosphate, Feed Grade | 1.8 |
| Calcium Carbonante (Ground Limestone) | 0.8 |
| Vitamin Premix TK-01 (1.03)[1] | 0.5 |
| Salt (NaCl) | 0.3 |
| Trace Mineral Premix TK-01 (1.02)[2] | 0.1 |
| Methionine Hydroxy Analog | 0.1 |
| Total | 100.0 |
| Broiler Grower | |
| Corn, Yellow, Ground | 57.7 |
| Soybean Meal, Solvent Extracted, Dehulled (50%) | 31.7 |
| Animal Fat (Beef tallow) | 6.0 |

| Ingredients | Percent |
|---|---|
| Dicalcium Phosphate, Feed Grade | 2.7 |
| Calcium Carbonante (Ground Limestone) | 0.9 |
| Vitamin Premix TK-01 (1.03)[1] | 0.5 |
| Salt (NaCl) | 0.2 |
| Methionine Hydroxy Analog | 0.2 |
| Trace Mineral Premix TK-01 (1.02)[2] | 0.1 |
| Total | 100.0 |
| Chick Starter, Light Breeds | |
| Corn, Yellow, Ground | 56.3 |
| Soybean Meal, Solvent Extracted, Dehulled (50%) | 17.9 |
| Wheat Middlings | 10.0 |
| Corn Distillers Dried Solubles | 5.0 |
| Fish Meal with Solubles | 5.0 |
| Alfalfa Meal, Dehydrated (17%) | 2.5 |
| Dicalcium Phosphate, Feed Grade | 1.3 |
| Calcium Carbonante | 0.9 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |
| Pullet Grower | |
| Corn, Yellow, Ground | 73.5 |
| Soybean Meal, Solvent Extracted, Dehulled (50%) | 21.9 |
| Dicalcium Phosphate, Feed Grade | 2.5 |
| Calcium Carbonante | 1.0 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |
| Pullet Developer | |
| Corn, Yellow, Ground | 67.5 |
| Oats, Ground Whole | 15.0 |
| Soybean Meal, Solvent Extracted, Dehulled (50%) | 13.4 |
| Dicalcium Phosphate, Feed Grade | 2.1 |
| Calcium Carbonante | 1.0 |
| Vitamin Premix[1] | 0.5 |
| Methionine Hydroxy Analog | 0.3 |
| Salt (NaCl) | 0.2 |
| Trace Mineral Premix[2] | 0.1 |
| Total | 100.0 |
| Turkey Starter | |
| Soybean Meal, Solvent Extracted, Dehulled (50%) | 40.7 |
| Corn, Yellow, Ground | 39.7 |
| Fish Meal with Solubles | 5.0 |
| Beef Tallow | 5.0 |
| Corn Distillers Dried Solubles | 2.5 |
| Alfalfa Meal, Dehydrated (17%) | 2.5 |
| Dicalcium Phosphate, Feed Grade | 2.5 |
| Calcium Carbonante | 1.2 |
| Vitamin Premix[1] | 0.5 |
| Salt (NaCl) | 0.2 |
| Trace Mineral Premix[2] | 0.1 |
| Methionine Hydroxy Analog | 0.1 |
| Total | 100.0 |
| Turkey Finisher | |
| Corn, Yellow, Ground | 71.2 |
| Soybean Meal, Solvent Extracted, Dehulled (50%) | 9.9 |
| Corn Distillers Dried Solubles | 5.0 |
| Alfalfa Meal, Dehydrated (17%) | 5.0 |
| Animal Fat | 3.0 |
| Fish Meal with Solubles | 2.5 |
| Dicalcium Phosphate, Feed Grade | 1.7 |
| Calcium Carbonante | 0.5 |
| Vitamin Premix[1] | 0.5 |
| Salt (NaCl) | 0.4 |
| Methionine Hydroxy Analog | 0.2 |
| Trace Mineral Premix[2] | 0.1 |

| Ingredients | Percent |
|---|---|
| Total | 100.0 |

[1] Vitamin premix provides 3000 IU of vitamin A, 900 ICU of vitamin D, 40 mg. of vitamin E, 0.7 mg. of vitamin K, 1000 mg. of choline, 70 mg. of niacin, 4 mg. of pantothenic acid, 4 mg. of riboflavin, 0.10 mg. of vitamin $B_{12}$, 0.10 mg. of biotin and 125 mg. of ethoxyquin per kg. of complete feed.
[2] Trace mineral premix provides 75 mg. of manganese, 50 mg. of zinc, 25 mg. of iron and 1 mg. of iodine per kg. of complete feed.

An anticoccidial combination of the invention can be admixed with any such poultry feedstuff so that the final feedstuff contains about 20 to about 500 grams of benzenamine per ton of feedstuff. For example, about 100 g. of 2,4-dinitro-N-[4-(1,1,2,2-tetrafluoroethoxy)phenyl]-6-(trifluoromethyl)benzenamine can be added to about one ton of the above-noted Broiler Grower mixture containing about 200 g. of narasin for use according to this invention. Similarly, about 100 g. of the benzenamine can be combined with about 400 g. of monensin or a monensin urethan derivative and the combination can be admixed to uniformity with about one ton of the above-described Turkey Finisher for administration to turkeys pursuant to the method of this invention.

The combinations defined above can alternatively be formulated as a feedstuff pre-mix. The term "feedstuff pre-mix" means a composition of the combination of the invention admixed with a suitable edible carrier, diluent or excipient, and if desired suitable binders, anti-dust agents and the like. For example, a benzenamine and lasalocid combination can be admixed with a substantially inert edible carrier such as ground rice hulls, soybean meal, wheat middlings, fermentation mycelia and the like. Nutritive carriers such as cereals can also be utilized. Binders such as starch, gelatin, soy protein and the like can be employed also. Anti-dust agents such as corn oil or soybean oil can also be incorporated at the rate of about 1 to 5 percent by weight. Such mixture of carrier and anticoccidial combination will preferably contain about 5 to about 90 percent by weight of the anticoccidial combination, and more preferably about 10 to about 70 percent by weight. An especially preferred premix will have a polyether antibiotic present in about 5 to about 10 percent by weight and a benzenamine in about 5 to about 10 percent by weight. A binder, if employed, is generally present in about 1 to about 5 percent by weight. Such pre-mix formulation is then mixed with a normal feed ration at a rate so that the active ingredient is present in about 1 to about 500 grams per ton of final feed ration.

Still another formulation which can be utilized according to this invention comprises a combination of this invention substantially dissolved in drinking water, for example in the drinking water of poultry such as chickens and turkeys. For such formulations, it is occasionally preferred to utilize physiologically-acceptable salts of each component, such as the sodium or potassium salts, which compounds generally are substantially water soluble. For such formulation, it is often convenient to prepare water-soluble powders or dispersible powders comprising a benzenamine-polyether combination admixed with carriers such as dextrose, sucrose, dimethyl sulfoxide, or other suitable diluent. Typically, the combination will be present in such forms in about 0.01 to about 30 percent by weight. Such powder or liquid formulations are conveniently added to the poultry drinking water at the site of administration.

The anticoccidial activity of the combinations of this invention has been determined in standard in vivo tests in chickens. Typical evaluations were conducted according to the following Examples:

EXAMPLE 1

One-week-old broiler chicks were alloted to cages holding five birds each. The animals were fed a medicated or control ration, typically for one day, prior to infection with oocysts of a coccidiosis-causing organism. The chicks were maintained on their respective rations for a period of time after infection, typically seven days. Generally, there were three replicates per treatment. Anticoccidial efficacy was typically determined by the lesion scores, both intestinal and cecal, but other measures of efficacy were employed in many of the tests. In determining lesion scores, the birds were sacrificed and the severity of lesions were scored on a 0–4 scale, with lesion-free birds scored as 0, extremely severe infections scored as 4, and intermediate degrees of infection scored as 1, 2, or 3. The scores of all birds which received a given treatment were averaged. (Intestinal lesions were scored in three areas of the gut so that total theoretical lesions for intestinal score is 12).

The following Tables present the results of tests carried out with various combinations of 2,4-dinitro-N-]4-(1,1,2,2-tetrafluoroethoxy)phenyl]-6-(trifluoromethyl)-benzenamine and monensin. Broiler chicks were innoculated with oocysts of *Eimeria tenella, Eimeria acervulina,* or *Eimeria maxima*. The results presented in the Tables are intestinal and cecal lesion scores measured seven days post treatment.

In the Tables, the data is reported with superscript letters. Data not followed by a common letter are significantly different ($p \leq 0.05$). The benzenamine employed in each experiment, and labelled in the Tables as "benzenamine", was 2,4-dinitro-N-]4-(1,1,2,2-(tetrafluoroethoxy)phenyl]-6-(trifluoromethyl)benzenamine.

TABLE 1

| benzenamine (ppm) | Intestinal Lesion Scores Monensin (ppm) | | | |
|---|---|---|---|---|
| | 0 | 25 | 50 | 100 |
| 0 | $5.60^d$ | $4.50^c$ | $0.90^{ab}$ | $0.00^a$ |
| 8 | $6.00^d$ | $0.87^{ab}$ | $0.00^a$ | |
| 15 | $1.87^b$ | $0.00^a$ | $0.00^a$ | |
| 30 | $0.20^a$ | | | |

TABLE 2

| benzenamine (ppm) | Cecal Lesion Scores Monensin (ppm) | | | |
|---|---|---|---|---|
| | 0 | 25 | 50 | 100 |
| 0 | $3.55^c$ | $3.50^c$ | $1.73^b$ | $0.00^a$ |
| 8 | $3.75^c$ | $2.87^c$ | $1.12^b$ | |
| 15 | $3.30^b$ | $1.73^b$ | $0.93^b$ | |
| 30 | $1.73^b$ | | | |

TABLE 3

| benzenamine (ppm) | Intestinal Lesion Scores Monensin (ppm) | | | |
|---|---|---|---|---|
| | 0 | 25 | 50 | 100 |
| 0 | $5.42^a$ | $3.00^b$ | $0.32^c$ | $0.00^c$ |
| 20 | $0.00^c$ | $0.00^c$ | $0.00^c$ | |
| 30 | $0.00^c$ | $0.00^c$ | $0.00^c$ | |

TABLE 3-continued

| benzenamine (ppm) | Intestinal Lesion Scores Monensin (ppm) | | | |
|---|---|---|---|---|
| | 0 | 25 | 50 | 100 |
| 40 | $0.00^c$ | | | |

TABLE 4

| benzenamine (ppm) | Cecal Lesion Scores Monensin (ppm) | | | |
|---|---|---|---|---|
| | 0 | 25 | 50 | 100 |
| 0 | $3.25^a$ | $3.10^a$ | $1.45^{bc}$ | $0.00^{de}$ |
| 20 | $2.00^b$ | $0.82^{ce}$ | $0.20^{de}$ | |
| 30 | $1.10^{cd}$ | $0.63^{ce}$ | $0.00^e$ | |
| 40 | $1.00^{cd}$ | | | |

As the data thus presented clearly indicates, the combinations provided by this invention are synergistic in the treatment of coccidial infections.

The combinations also cause a beneficial affect on weight gain of animals. For example, poultry receiving the combinations gain more weight than when receiving the individual components, and also exhibit a better feed to gain ratio. The following data demonstrates the improved weight gain and feed utilization efficiency of broiler cockerels when receiving a combination of monensin sodium salt and 2,4-dinitro-N-[4-(1,1,2,2-tetrafluoroethoxy)phenyl]-6-(trifluoromethyl)benzenamine.

TABLE 5

| benzenamine (ppm) | Average survivor weight gain in grams Monensin (ppm) | | | |
|---|---|---|---|---|
| | 0 | 25 | 50 | 100 |
| 0 | 162.1 | 165.7 | 207.9 | 217.8 |
| 20 | 205.6 | 220.8 | 216.6 | |
| 30 | 220.8 | 194.8 | 203.8 | |
| 40 | 186.8 | | | |

TABLE 6

| benzenamine (ppm) | Average survivor weight gain in grams Monensin (ppm) | | | |
|---|---|---|---|---|
| | 0 | 25 | 50 | 100 |
| 0 | 106.9 | 173.8 | 226.0 | 228.7 |
| 8 | 138.2 | 216.1 | 236.2 | |
| 15 | 180.1 | 221.7 | 228.5 | |
| 30 | 205.0 | | | |

TABLE 7

| benzenamine (ppm) | Average feed/gain Monensin (ppm) | | | |
|---|---|---|---|---|
| | 0 | 25 | 50 | 100 |
| 0 | 1.633 | 1.973 | 1.787 | 1.680 |
| 20 | 1.796 | 1.709 | 1.726 | |
| 30 | 1.655 | 1.793 | 1.781 | |
| 40 | 1.953 | | | |

TABLE 8

| benzenamine (ppm) | Average feed/gain Monensin (ppm) | | | |
|---|---|---|---|---|
| | 0 | 25 | 50 | 100 |
| 0 | 2.900 | 1.964 | 1.737 | 1.596 |
| 8 | | 1.715 | 1.615 | |
| 15 | 1.863 | 1.635 | 1.623 | |
| 30 | 1.796 | | | |

As pointed out above, the combinations provided by this invention are preferably formulated and supplied as poultry feedstuff premix compositions. The following examples illustrate typical premix compositions provided by the invention.

EXAMPLE 2

Feedstuff Premix Composition

| Ingredient | Percent by Weight |
|---|---|
| Monensin sodium | 5.0 |
| 2,4-dinitro-N—[4-(1,1,2,2-tetrafluoroethoxy)phenyl]-6-(trifluoromethyl)benzenamine | 5.0 |
| Starch | 2.0 |
| Soybean oil | 1.0 |
| Wheat middlings | 87.0 |
| | 100.0 |

The above ingredients are blended to uniformity to provide a premix having about 45 grams of active ingredient per pound. The premix is then thoroughly mixed with a feed ration such as Pullet Grower at the rate of about 2 to about 3 pounds per ton of feed.

EXAMPLE 3

Feedstuff Premix Composition

| Ingredient | Percent by Weight |
|---|---|
| Monensin 4-bromophenylurethan | 8.0 |
| 2,4-dinitro-N—[4-(trifluoromethoxy)phenyl]-6-(trifluoromethyl)benzenamine | 5.0 |
| Cellulose | 3.0 |
| Corn oil | 2.0 |
| Rice hulls | 30.0 |
| Milo flour | 52.0 |
| | 100.0 |

The above ingredients are blended to uniformity to provide a poultry premix having about 59 grams of active combination per pound of premix. The premix is then mixed thoroughly with a feedstuff such as Turkey Finisher at the rate of about 2 pounds per ton.

We claim:

1. A combination useful in the treatment of coccidiosis in animals comprising in synergistic amounts from about 1 to about 10 parts by weight of a polyether antibiotic and about 10 to about 1 part by weight of a benzenamine selected from 2,4-dinitro-N-[4-(trifluoromethoxy)phenyl]-6-(trifluoromethyl)benzenamine; 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine.

2. The combination of claim 1 wherein the polyether antibiotic is selected from the group consisting of monensin, monensin phenylurethane derivatives, A204, lasalocid, dianemycin, nigericin, X-206, ionomycin, laidlomycin, grisorixin, lenoremycin, narasin, salinomycin, lonomycin, alborixin, septamycin, etheromycin, mutalamycin and calcimycin.

3. The combination according to claim 2 wherein the polyether antibiotic employed is selected from the group consisting of monensin, monensin 4-bromophenylurethan, narasin, lasalocid, salinomycin, A-204, lonomycin, X-206, nigericin and dianemycin.

4. The combination according to claim 3 wherein the polyether antibiotic employed is monensin.

5. The combination according to claim 3 wherein the polyether antibiotic employed is narasin.

6. The combination according to claim 3 wherein the polyether antibiotic employed is lasalocid.

7. The combination according to claim 3 where the polyether antibiotic employed is monensin 4-bromophenylurethan.

8. A poultry feedstuff premix composition comprising a combination of claim 1 admixed with a suitable edible carrier, diluent or excipient.

9. The poultry feedstuff premix of claim 8 comprising monensin in a concentration of about 5 to about 10 percent by weight and 2,4-dinitro-N-[4-(1,1,2,2-tetrafluoroethoxy)phenyl]-6-(trifluoromethyl)benzenamin ein a concentration of about 5 to about 10 percent by weight.

10. The poultry feedstuff premix of claim 8 comprising monensin 4-bromophenylurethan in a concentration of about 5 to about 10 percent weight and 2,4-dinitro-N-[4-(1,1,2,2-tetrafluoroethoxy)phenyl]-6-(trifluoromethyl)benzenamine in a concentration of about 5 to about 10 percent by weight.

11. A method for controlling coccidiosis in animals comprising administering to the animal an anticoccidial amount of the combination of claim 1.

12. The method according to claim 11 wherein the animal species treated is poultry.

13. The method according to claim 12 wherein the combination is administered orally.

14. The method according to claim 13 employing the combination wherein the polyether antibiotic is monensin.

15. The method according to claim 13 employing a combination wherein the polyether antibiotic is monensin 4-bromophenylurethan.

16. The method according to claim 14 employing a combination wherein the benzenamine is 2,4-dinitro-N-[4-(1,1,2,2-tetrafluoroethoxy)phenyl]-6-(trifluoromethyl)benzenamine.

17. The method according to claim 15 employing a combination wherein the benzenamine is 2,4-dinitro-N-[4-(1,1,2,2-tetrafluoroethoxy)phenyl]-6-(trifluoromethyl)benzenamine.

* * * * *